(12) United States Patent
Yang et al.

(10) Patent No.: US 11,592,505 B2
(45) Date of Patent: Feb. 28, 2023

(54) INTEGRATED MAGNETIC RESONANCE IMAGING (MRI) COIL

(71) Applicant: Quality Electrodynamics, LLC, Mayfield Village, OH (US)

(72) Inventors: Xiaoyu Yang, Indiana, PA (US); Haoqin Zhu, Mayfield Village, OH (US); Tsinghua Zheng, Chesterland, OH (US)

(73) Assignee: Quality Electrodynamics, LLC, Mayfield Village, OH (US)

( * ) Notice: Subject to any disclaimer, the term of this patent is extended or adjusted under 35 U.S.C. 154(b) by 705 days.

(21) Appl. No.: 16/565,954

(22) Filed: Sep. 10, 2019

(65) Prior Publication Data

US 2020/0081081 A1    Mar. 12, 2020

Related U.S. Application Data

(60) Provisional application No. 62/729,678, filed on Sep. 11, 2018.

(51) Int. Cl.
*A61B 5/055* (2006.01)
*G01R 33/34* (2006.01)
*G01R 33/30* (2006.01)
*G01R 33/3415* (2006.01)

(52) U.S. Cl.
CPC ........ *G01R 33/34084* (2013.01); *A61B 5/055* (2013.01); *G01R 33/34007* (2013.01); *G01R 33/3415* (2013.01)

(58) Field of Classification Search
CPC ............ G01R 33/34084; G01R 33/341; G01R 33/3415
See application file for complete search history.

(56) References Cited

U.S. PATENT DOCUMENTS

| | | | |
|---|---|---|---|
| 4,825,162 A | 4/1989 | Roemer et al. | |
| 2008/0129293 A1* | 6/2008 | Schnell | G01R 33/341 324/318 |
| 2009/0009172 A1* | 1/2009 | Feld | A61B 5/055 324/321 |
| 2013/0320981 A1* | 12/2013 | Bulumulla | G01R 33/34007 324/318 |
| 2015/0168511 A1* | 6/2015 | Jeong | G01R 33/3415 324/321 |
| 2017/0299669 A1* | 10/2017 | Hesels | G01R 33/30 |

* cited by examiner

*Primary Examiner* — Colin T. Sakamoto
(74) *Attorney, Agent, or Firm* — Eschweiler & Potashnik, LLC (57) ABSTRACT

Embodiments relate to integrated MRI (Magnetic Resonance Imaging) coil arrays that can be stored within a patient table when not in use. One example embodiment comprises a coil array comprising: at least one flat spine-like coil array arranged within a patient table of a MRI system; and flexible coil array(s) configured to be in a stored position within the patient table, wherein, in the stored position, the flexible coil array(s) are one of within or under the at least one flat spine-like rigid coil array, wherein the flexible coil array(s) are further configured to be in an extended position, wherein, in the extended position, the flexible coil array(s) is configured to be extracted from the patient table and to wrap around at least one anatomical region of a patient on the patient table to facilitate MRI of the at least one anatomical region.

20 Claims, 7 Drawing Sheets

INTEGRATED MAGNETIC RESONANCE IMAGING (MRI) COIL

REFERENCE TO RELATED APPLICATIONS

This application claims the benefit of U.S. Provisional Patent Applications No. 62/729,678 filed Sep. 11, 2018, entitled "INTEGRATED MAGNETIC RESONANCE IMAGING (MRI) COIL", the contents of which are herein incorporated by reference in their entirety.

BACKGROUND

Magnetic resonance imaging (MRI) involves the transmission and receipt of radio frequency (RF) energy. RF energy may be transmitted by a coil. Resulting magnetic resonance (MR) signals may also be received by a coil. In early MRI, RF energy may have been transmitted from a single coil and resulting MR signals received by a single coil. Later, multiple receivers may have been used in parallel acquisition techniques. Similarly, multiple transmitters may have been used in parallel transmission (pTx) techniques.

RF coils create the $B_1$ field that rotates the net magnetization in a pulse sequence. RF coils may also detect precessing transverse magnetization. Thus, RF coils may be transmit (Tx) coils, receive (Rx) coils, or transmit and receive (Tx/Rx) coils. An imaging coil should be able to resonate at a selected Larmor frequency. Imaging coils include inductive elements and capacitive elements. The inductive elements and capacitive elements have been implemented according to existing approaches using two terminal passive components (e.g., capacitors). The resonant frequency, f, of a RF coil is determined by the inductance (L) and capacitance (C) of the inductor capacitor circuit according to equation (1):

$$f = \frac{1}{2\pi\sqrt{LC}} \quad (1)$$

Imaging coils may need to be tuned. Tuning an imaging coil may include varying the value of a capacitor. Recall that frequency: $f=\omega/(2\pi)$, wavelength in vacuum: $\lambda=c/f$, and $\lambda=4.7$ m at 1.5 T. Recall also that the Larmor frequency: $f_0\gamma B_0(2\pi)$, where (for $^1$H nuclei) $\gamma/(2\pi)=42.58$ MHz/T; at 1.5 T, $f_0=63.87$ MHz; at 3 T, $f_0=127.73$ MHz; at 7 T, $f_0=298.06$ MHz. Basic circuit design principles include the fact that capacitors add in parallel (impedance $1/(jC\omega)$) and inductors add in series (impedance $jL\omega$).

DETAILED DESCRIPTION

The present disclosure will now be described with reference to the attached drawing figures, wherein like reference numerals are used to refer to like elements throughout, and wherein the illustrated structures and devices are not necessarily drawn to scale.

Figure 1:
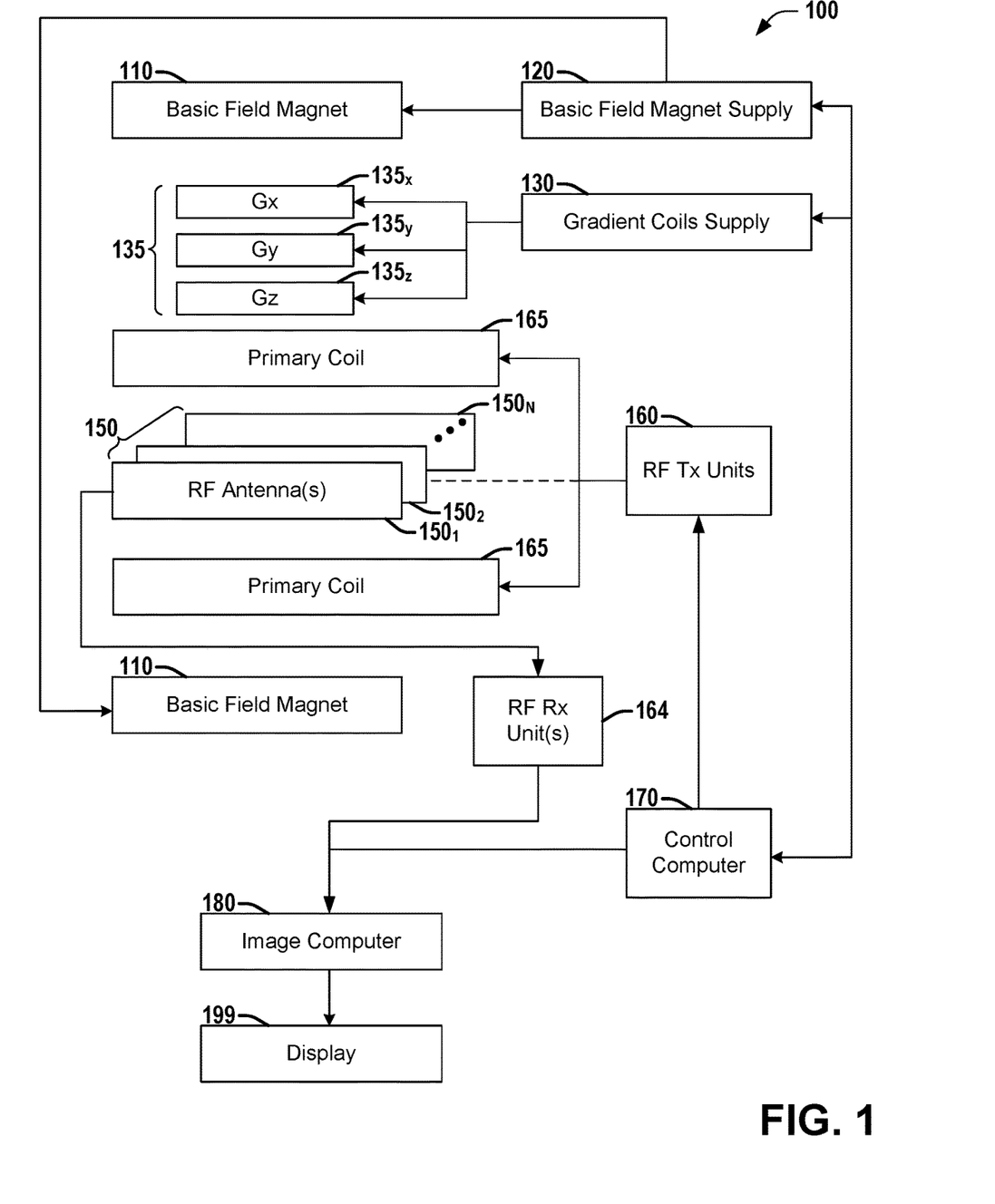
FIG. 1 is a block diagram illustrating an example MRI (Magnetic Resonance Imaging) apparatus that can be configured with example MRI RF (Radio Frequency) coils, coil elements, coil arrays, or circuitry according to one or more embodiments described herein.

Embodiments described herein can be implemented in a MRI (Magnetic Resonance Imaging) system using any suitably configured hardware and/or software. Referring to FIG. 1, illustrated is an example MRI apparatus 100 that can be configured with example MRI RF coils, coil elements, coil arrays, or circuitry according to one or more embodiments described herein. Apparatus 100 includes basic field magnet(s) 110 and a basic field magnet supply 120. Ideally, the basic field magnets 110 would produce a uniform $B_0$ field. However, in practice, the $B_0$ field may not be uniform, and may vary over an object being imaged by the MRI apparatus 100. MRI apparatus 100 can include gradient coils 135 configured to emit gradient magnetic fields like $G_x$ (e.g., via an associated gradient coil 135$_x$), $G_y$ (e.g., via an associated gradient coil 135$_y$) and $G_z$ (e.g., via an associated gradient coil 135$_z$). The gradient coils 135 can be controlled, at least in part, by a gradient coils supply 130. In some examples, the timing, strength, and orientation of the gradient magnetic fields can be controlled, and thus selectively adapted during an MRI procedure.

MRI apparatus 100 can include a primary coil 165 configured to generate RF pulses. The primary coil 165 can be a whole body coil (WBC). The primary coil 165 can be, for example, a birdcage coil. The primary coil 165 can be controlled, at least in part, by a RF transmission unit 160. RF transmission unit 160 can provide a signal to primary coil 165.

MRI apparatus 100 can include a set of RF antennas 150 (e.g., one or more RF antennas 150$_1$-150$_N$, which can be as described herein). RF antennas 150 can be configured to generate RF pulses and/or to receive resulting magnetic resonance signals from an object to which the RF pulses are directed. A RF antenna 150 configured solely to generate RF pulses can be referred to herein as a transmit (or Tx) antenna (or coil or coil array), while a RF antenna 150 configured solely to receive resulting magnetic resonance signals from an object to which the RF pulses are directed can be referred to herein as a receive (or Rx) antenna (or coil or coil array), and a RF antenna 150 configured to both generate RF pulses and receive resulting magnetic resonance signals can be referred to herein as a transmit/receive (or Tx/Rx) antenna (or coil or coil array). Unless otherwise indicated, antennas, coils, and coil arrays discussed herein can, in various embodiments, be any of a Tx antenna/coil/coil array, a Rx antenna/coil/coil array, or a Tx/Rx antenna/coil/coil array.

In some embodiments, RF antennas 150 can be configured to inductively couple with primary coil 165 and generate RF pulses and to receive resulting magnetic resonance signals from an object to which the RF pulses are directed. In other embodiments, RF antennas 150 can be electrically coupled to a power source (e.g., RF Tx unit 160) that can drive RF antennas 150 to generate RF pulses, and RF antennas can also be configured to receive resulting magnetic resonance signals from an object to which the RF pulses are directed. In one embodiment, one or more members of the set of RF antennas 150 can be fabricated from flexible coaxial cable, or other conductive material. The set of RF antennas 150 can be connected with a RF receive unit 164.

The gradient coils supply 130 and the RF transmission units 160 can be controlled, at least in part, by a control computer 170. The magnetic resonance signals received from the set of RF antennas 150 can be employed to generate an image, and thus can be subject to a transformation process like a two dimensional fast Fourier transform (FFT) that generates pixilated image data. The transformation can be performed by an image computer 180 or other similar processing device. The image data can then be shown on a display 199. RF Rx Units 164 can be connected with control computer 170 or image computer 180. While FIG. 1 illustrates an example MRI apparatus 100 that includes various components connected in various ways, it is to be appreciated that other MRI apparatus can include other components connected in other ways, and can be employed in connection with various embodiments discussed herein.

In one embodiment, MRI apparatus 100 includes control computer 170. In one example, a member of the set of RF antennas 150 can be individually controllable by the control computer 170. A member of the set of RF antennas 150 can be an example MRI RF coil array including, for example, MRI RF coil arrays as described herein. In various embodiments, the set of RF antennas 150 can include various combinations of example embodiments of MRI RF coil arrays, elements or example embodiments of MRF RF coil arrays, including single-layer MRI RF coil elements or single-layer MRI RF coil arrays, according to various embodiments described herein.

An MRI apparatus can include, among other components, a controller (e.g., control computer 170) and a RF coil (e.g., primary coil 165) operably connected to the controller. The controller can provide the RF coil with a current, a voltage, or a control signal. The coil can be a whole body coil. The coil can inductively couple with an example MRI RF coil element, or MRI RF coil array, as described herein. Control computer 170 can provide a DC bias current, or control a DC bias control circuit to control the application of a DC bias current to MRI RF coil arrays or elements that can be part of antennas 150.

A phase array coil is one existing coil technology that can be employed to build a multiple-channel MR (Magnetic Resonance) coil. Such coils have the advantage of providing large-coil-like signal penetration while having the high signal performance of a small coil at shallow depth. Phase array coils are used in many MR receiving coils.

Flexible MR array coils have also been used in many MRI coils, and have their own advantages in work flow and patient comfort. For example, a flexible torso coil can be put directly on top of a patient body and conform to the body to minimize the distance between the patient. Another example is that a flexible coil can also be wrapped around knee or hand/wrist or shoulder as a generic coil. However, one disadvantage of a flexible coil in existing systems is that a flexible coil has a thick cable connected to the coil. Even though the coil itself is light and easy to manage, the thick cable negates the flexible coil advantage in existing systems. To overcome this issue, wireless coils have been proposed to eliminate the cable. However, there are other disadvantages to wireless coils, such as significantly more electronics, additional power electronics, etc. In various embodiments, systems and techniques discussed herein can reduce issues arising from the thick cable of flexible coils and achieve a "wireless-like" coil.

Figure 2:
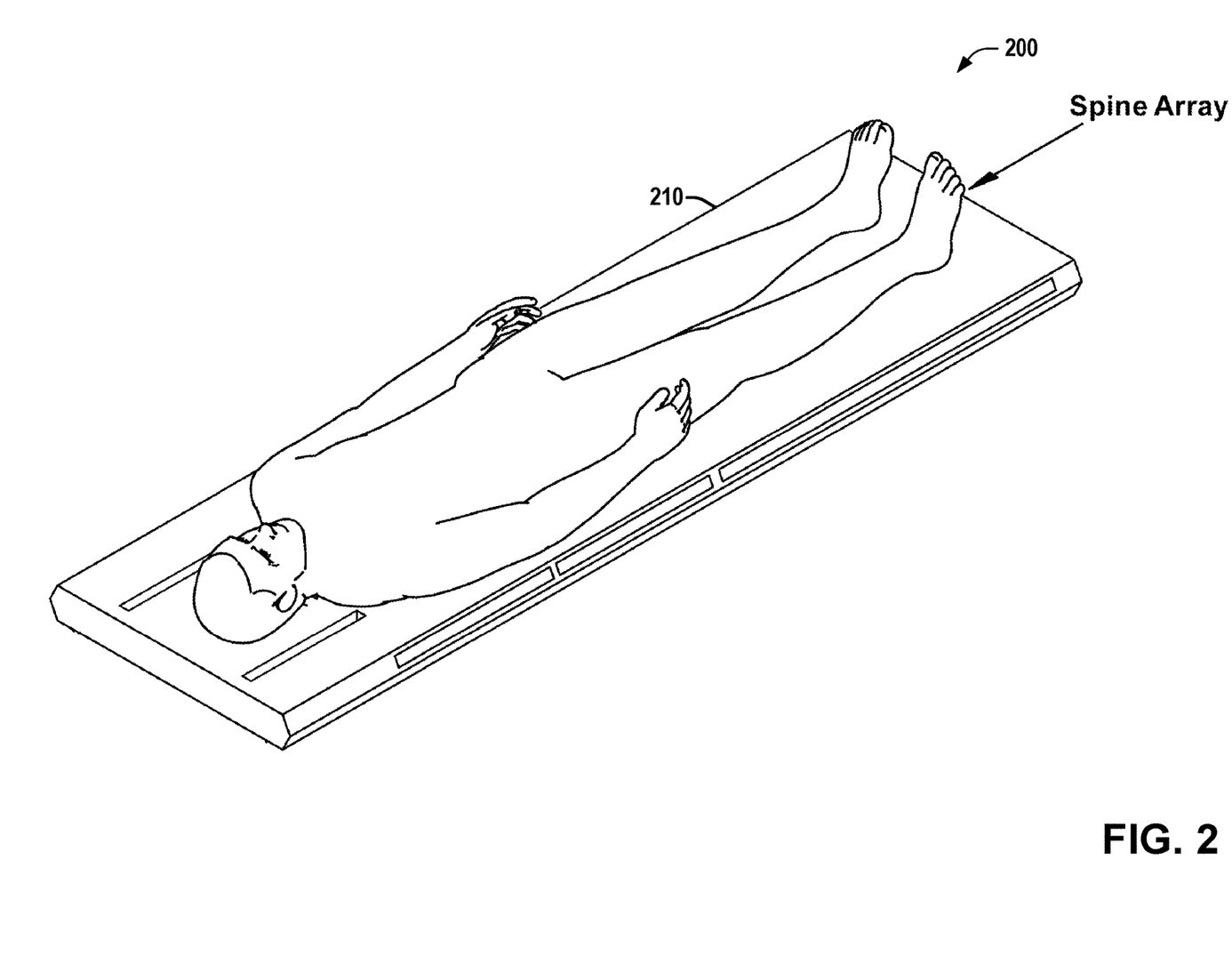
FIG. 2 is a diagram illustrating an example patient table comprising a spine array coil, in connection with various aspects discussed herein.

Various embodiments can be employed as or in connection with spine array coils, instead of an existing rigid spine array coil. Referring to FIG. 2, illustrated is a diagram showing an example patient table comprising a spine array coil 210, in connection with various aspects discussed herein. Unlike other coils, the spine coil 210 is a special coil which stays on the patient table 200 in most scenarios. Although the terminology "spine coil," "spine array coil," or similar terminology, as used herein, can refer to a coil on or in a patient table that (either alone or in combination with other coil(s) on or in the patient table) covers an area underneath one or more of a patient's spine, head, or legs and feet. In existing systems, a spine coil 210 can be always connected to the MRI system in most such systems and/or can be part of the patient table 200.

Figure 3:
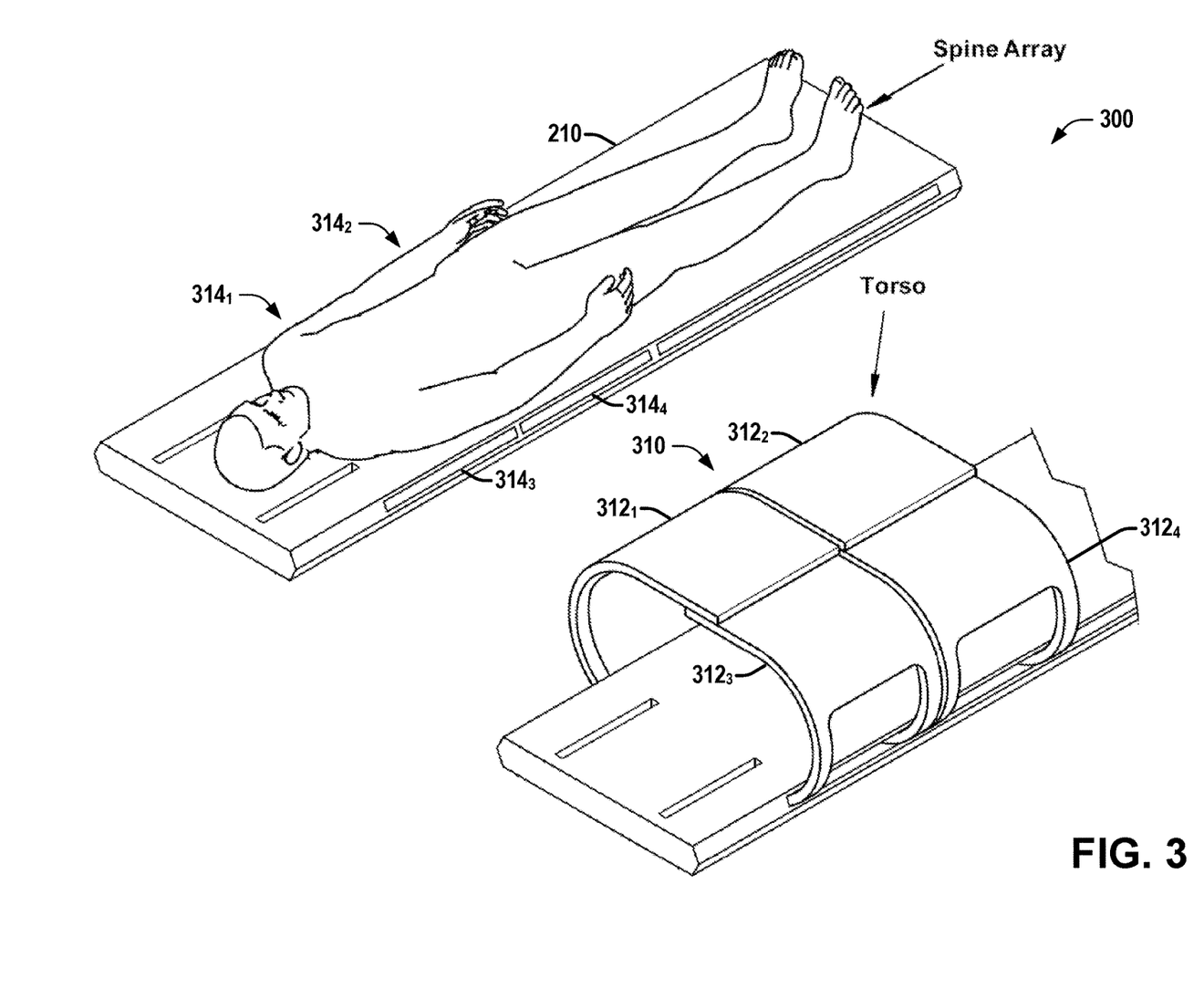
FIG. 3 is a diagram illustrating a first example system comprising a first example flexible coil array that can be stored under or within a spine coil array of a MRI system, according to various aspects discussed herein.

In various embodiments, at least one flexible coil array can be stored under or within a spine coil array. Referring to FIG. 3, illustrated is a diagram showing a first example system 300 comprising a first example flexible coil array 310 (e.g., employable as a RF antenna 150) that can be stored under or within a spine coil array 210 of a MRI system, according to various aspects discussed herein. If a MRI operator wants to do spine imaging, various embodiments can disable (e.g., automatically, based on operator input, etc.) flexible array coil 310 so that the flexible array coil 310 will not interfere with imaging from the spine coil 210. In various embodiments, the disabling mechanism can comprise one or more of a PIN diode switch, a MEMS switch, a low or high input impedance preamplifier, a FET switch, and/or an optical switch. If a MRI operator wants to do torso imaging, the operator can take the one or more flexible coil portion(s) $312_i$ hidden in or under the spine coil 210 and wrap them around the patient torso as a torso coil (e.g., flexible coil 310) and perform a torso scan. After the scan is done, the portions $312_i$ of flexible coil 310 can be retracted back to its storage places via openings $314_i$ on the two opposite long sides of the patient table, such that system 300 can perform spine imaging via spine coil 210. In various embodiments, flexible coil 310 can be part of spine coil 210, while in other embodiments, flexible coil 310 can be stored under spine coil 210 when not in use. Although in FIG. 3 coil array 310 is shown as comprising four portions $312_1$-$312_4$, in various embodiments, flexible coil arrays of the double-sided construction of coil array 310 (wherein each portion $312_i$ on the left side of the patient body has a corresponding portion $312_{N+i}$ on the right side of the patient body) can have any even number of portions $312_i$ (e.g., 2N where N is a positive integer, such as 2, 4, 6, 8, etc.). In various embodiments, each coil array portion can comprise one or more coil array elements, and corresponding left and right portions $312_i$ can together form a row of coil array elements of coil array 310 when extended for torso scanning. In embodiments wherein coil array 310 comprises more than two portions $312_i$, adjacent rows can be configured to partially overlap (such that coil elements within coil array portions $312_i$ of adjacent rows partially overlap), underlap (such that bottom and top edges of coil elements within coil array portions $312_i$ of adjacent rows are offset by some non-zero distance), etc. In some embodiments, spine coil array 210 and/or flexible coil array (e.g., flexible coil array 310 or other flexible coil arrays discussed herein) can be permanently connected (e.g., electrically and mechanically) to a MRI system (e.g., via the patient table). Alternatively, in other embodiments, spine coil array 210 and/or flexible coil array (e.g., flexible coil array 310 or other flexible coil arrays discussed herein) can be removably connected (e.g., electrically and mechanically) to the MRI system (e.g., via the patient table), and can be configured to connect to any of a plurality of MRI systems (e.g., MRI systems of one or more designs, etc.). Thus, in some embodiments, the flexible coil can be attached to the table via the flexible coil being integrated into the patient table mechanically, while in other embodiments, the flexible coil can be a separate apparatus (e.g., an independent flexible coil with its own housing) that can be placed on top of the patient table and under spine coil array 210 and thereby can be removably attached to the MRI system.

Figure 4:
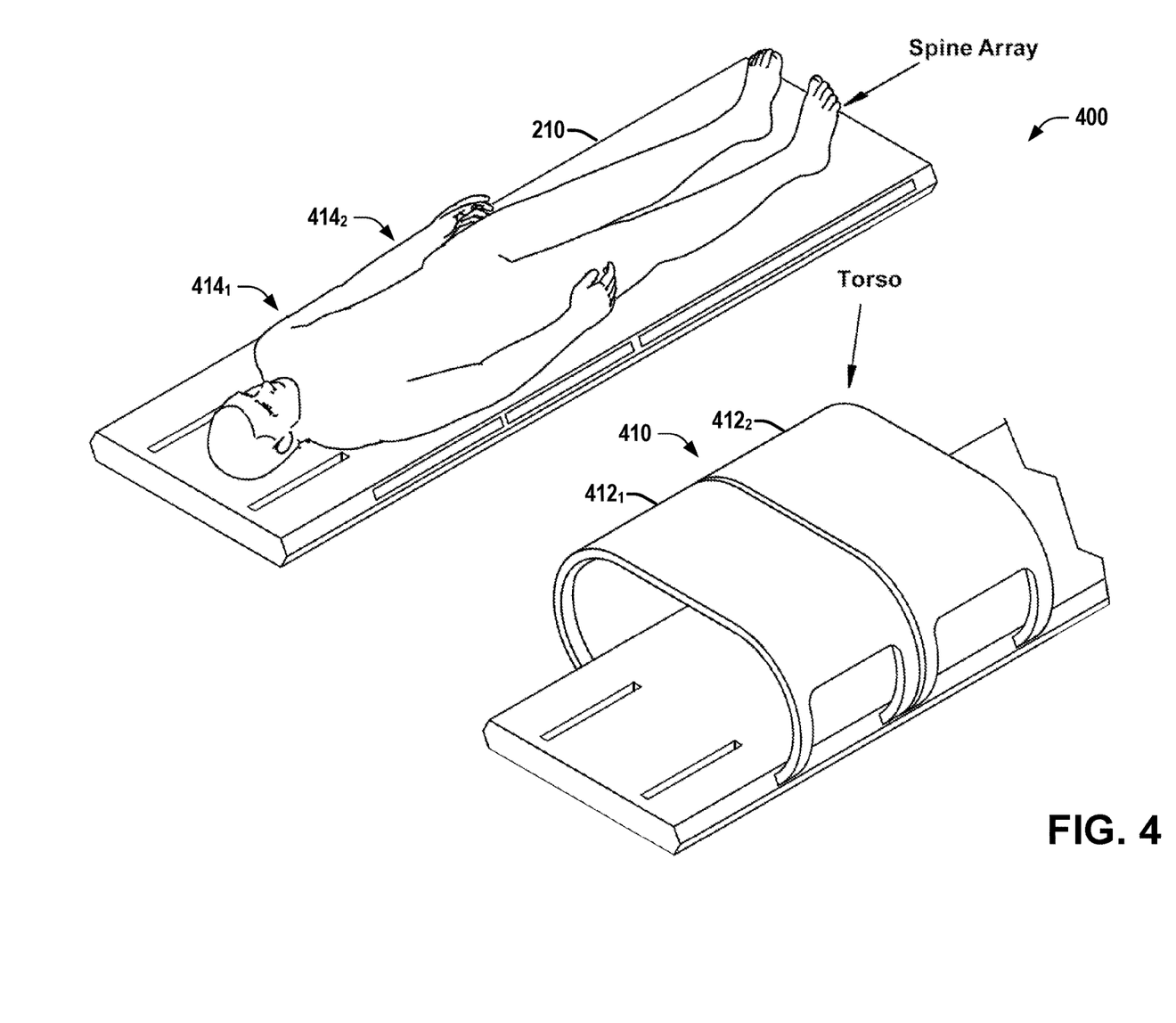
FIG. 4 is a diagram illustrating a second example system comprising a second example flexible coil array that can be stored under or within a spine coil array of a MRI system, according to various aspects discussed herein.

Referring to FIG. 4, illustrated is a diagram showing a second example system 400 comprising a second example flexible coil array 410 (e.g., employable as a RF antenna 150) that can be stored under or within a spine coil array 210 of a MRI system, according to various aspects discussed herein. Flexible coil 410 (and similar embodiments) can comprise one or more portion(s) $412_i$ that can be taken from openings $414_i$ on a single side of the table comprising spine array 210, and flexible coil 410 can be long enough to cover the human torso in left right direction. In contrast, flexible coil 310 (and similar embodiments) can comprise one or more portion(s) $312_i$ that can be taken from openings $314_i$ on both sides of spine coil 210, wherein left and right portions $312_i$ can be about 50% the length of the single side coil 410. Similar to coil array 310 of FIG. 3, coil array 410 of FIG. 4 can comprise any positive number (e.g., N, for N a positive integer) of array portions $412_i$, each of which can comprise a row of one or more coil array elements of coil array 310 when extended for torso scanning, and embodiments with more than one row can have adjacent rows overlap, underlap, etc.

Figure 5:
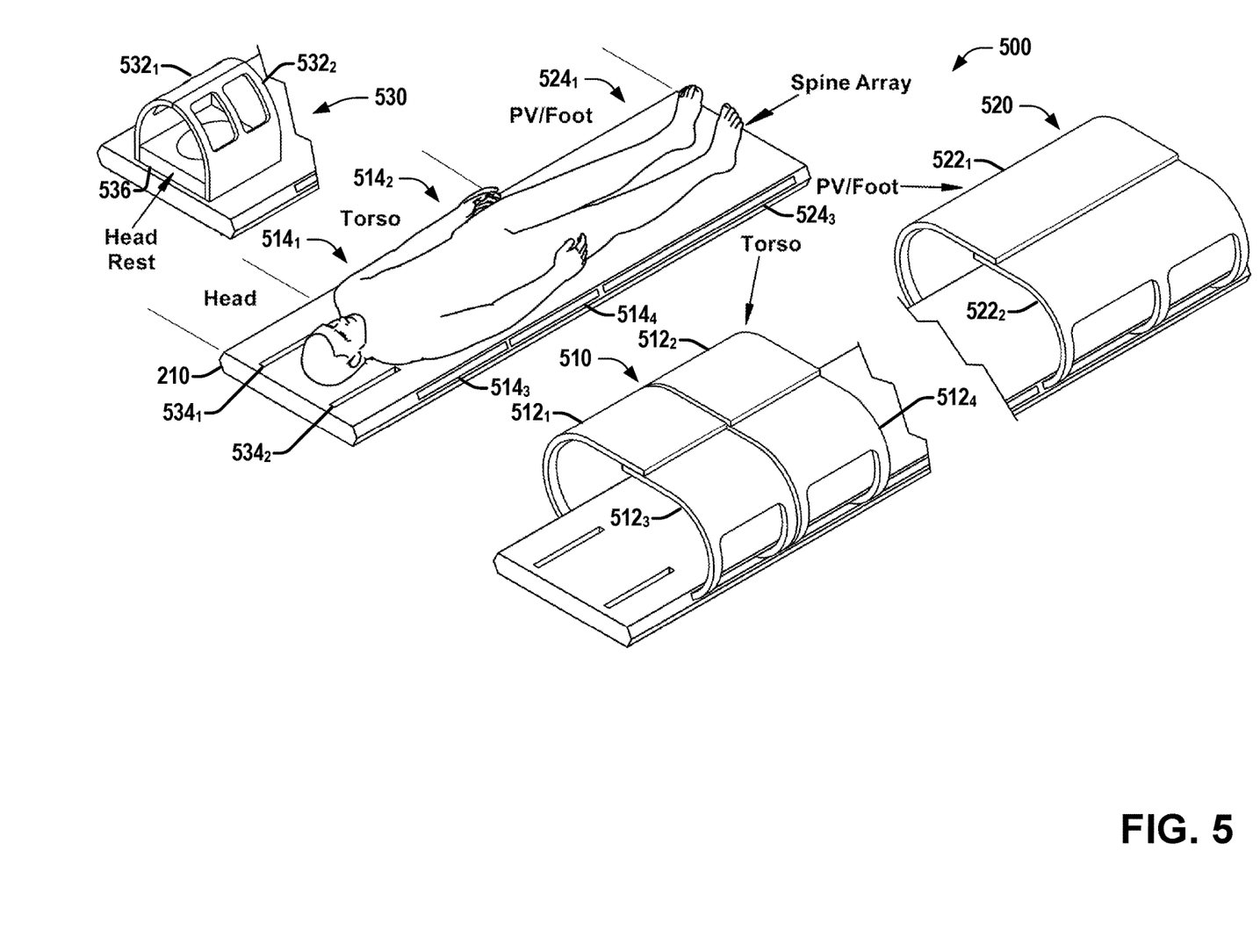
FIG. 5 is a diagram illustrating an example system comprising a plurality of example flexible coil arrays that can be stored under or within a spine coil array of a MRI system, according to various aspects discussed herein.

Because spine coil 210 is long and the human body is not uniform along the superior and inferior direction, in various embodiments, multiple flexible coils along the SI (Superior-Inferior) direction can be stored under or in the spine coil 210. Referring to FIG. 5, illustrated is a diagram showing an example system 500 comprising a plurality of example flexible coil arrays 510, 520, and 530 (e.g., each of which are employable as a RF antenna 150) that can be stored under or within a spine coil array 210 of a MRI system, according to various aspects discussed herein. FIG. 5 shows three possible flexible coil arrays that can be stored within or under a spine coil array 210: a first flexible coil array 510, comprising segments $512_i$ that can be accessed via openings $514_i$, which can be employed as a torso coil; a second flexible coil array 520, comprising segments $522_i$ that can be accessed via openings $524_i$, which can be employed as a peripheral vascular and/or foot coil; and a third flexible coil array 530, comprising segments $532_i$ that can be accessed via openings $534_i$, which can be employed as a head coil (and in connection with which an optional head rest 536 can be employed for patient comfort and/or head positioning). Although in FIG. 5, each flexible array coil 510, 520, and 530 is shown with a double-sided design like flexible array coil 310, in various embodiments, one or more of flexible array coil 510, 520, or 530 can alternatively employ a single-sided design like flexible array coil 410. Additionally, although specific number of coil array portions $512_i$ (two on each side), $522_i$ (one on each side), and $532_i$ (one on each side), in various embodiments, other numbers of coil array portions $512_i$, $522_i$, and/or $532_i$ can be employed than shown in FIG. 5 (e.g., any positive integer number of portions in a single-sided coil array 510, 520, and/or 530, and any positive even number of portions in a double-sided coil array 510, 520, and/or 530).

Figure 6:
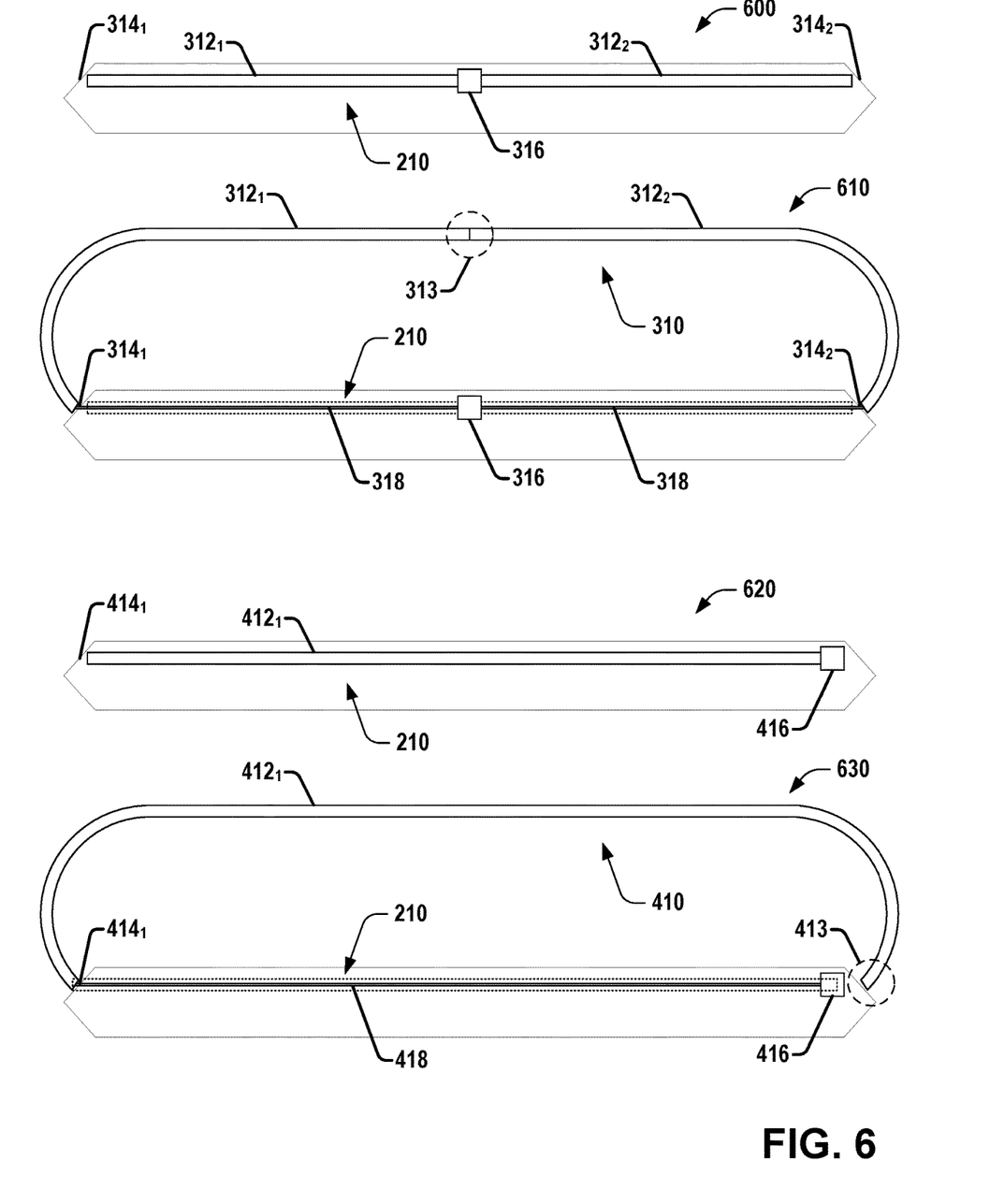
FIG. 6 is a diagram illustrating cross sectional views of a patient table for various embodiments wherein portions of a flexible coil array are stored within or as part of a spine coil array, according to various aspects discussed herein.
Figure 7:
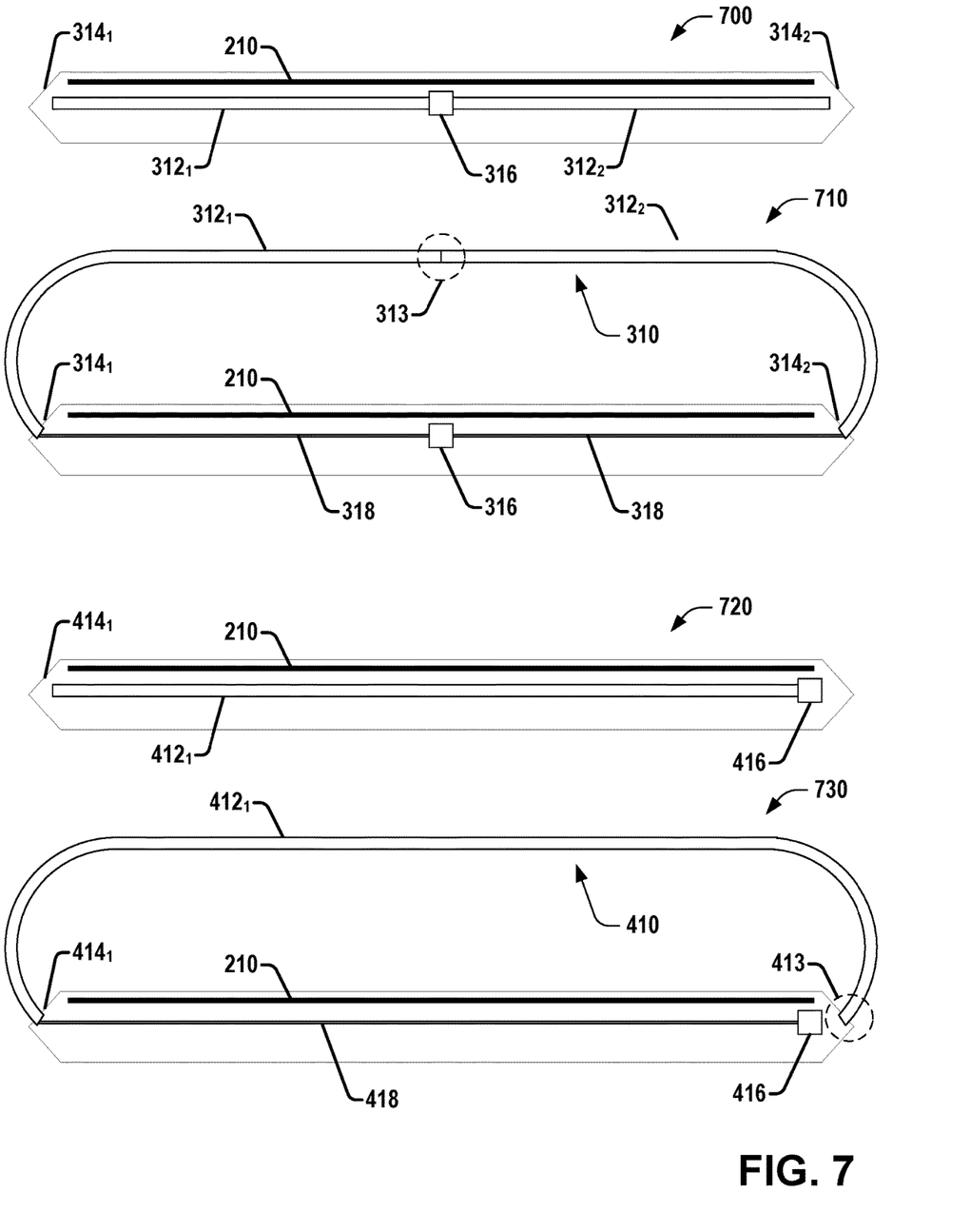
FIG. 7 is a diagram illustrating cross sectional views of a patient table for various embodiments wherein portions of a flexible coil array are stored under a spine coil array, according to various aspects discussed herein.

Referring to FIG. 6, illustrated are cross sectional views of a patient table for various embodiments wherein portions of a flexible coil array (e.g., 310, 410, 510, 520, 530) are stored within or as part of a spine coil array 210, according to various aspects discussed herein. Referring to FIG. 7, illustrated are cross sectional views of a patient table for various embodiments wherein portions of a flexible coil array (e.g., 310, 410, 510, 520, 530) are stored under a spine coil array 210, according to various aspects discussed herein. At 600 and 620, portions $312_i$ of a double-sided flexible coil array 310 and $412_i$ of a single-sided flexible coil array 410 are shown in a stored position within a spine coil array 210. Similarly, at 700 and 720, portions $312_i$ of a double-sided flexible coil array 310 and $412_i$ of a single-sided flexible coil array 410 are shown in a stored position under a spine coil array 210.

In the embodiments of both FIG. 6 and FIG. 7, connectors 316 (for double-sided embodiments) and 416 (for single-sided embodiments) can both electrically connect portions $312_i$ and $412_i$ to receive circuitry (e.g., one or more RF Rx units 164) and/or transmit circuitry (e.g., via electrical and/or inductive coupling to one or more RF Tx units 164) of an MRI system and secure portions $312_i$ and $412_i$ to the patient table in both extended and stored (or retracted) positions. In various embodiments, connector 316 and/or connector 416 can comprise a retraction mechanism (e.g., spring, elastic, etc.) to facilitate returning portions $312_i$ and $412_i$ to a stored (retracted, etc.) position for storage. Additionally, in various embodiments, connector 316 and/or connector 416 can comprise a disabling mechanism (e.g., of any variety discussed herein, etc.) that can facilitate disabling the electrical connection between portions $312_i$ and $412_i$, respectively, and receive and/or transmit circuitry of the MRI system when flexible coil array 310 and/or 410, respectively, are not in use, and can also, in various embodiments, facilitate disabling the electrical connection between spine coil array 210 and the receive and/or transmit circuitry of the MRI system when flexible coil array 310 and/or 410, respectively, are in use.

At 610, 630, 710, and 730, portions $312_i$ of a double-sided flexible coil array 310 and $412_i$ of a single-sided flexible coil array 410 are shown in an extended position to form coil arrays 310 and 410, respectively. As can be seen in FIGS. 6 and 7, in various embodiments, cables 318 and 418 connecting portions $312_i$ and $412_i$ flexible coil arrays 310 and 410, respectively, to connectors 316 and 416 can remain within the patient table where it does not interfere with an operator of the MRI system. Additionally, in the extended position, a securing mechanism 313 (e.g., buttons, straps, hook and loop fasteners such as Velcro®, etc.) can be used to connect portions $312_i$ to each other and maintain portions $312_i$ in their extended position during imaging via coil array 310, and similarly, a securing mechanism 413 (e.g., buttons, straps, hook and loop fasteners such as Velcro®, etc.) can be used to connect portion(s) $412_i$ to the patient table and maintain portion(s) $412_i$ in their extended position during imaging via coil array 410. In various embodiments, such securing mechanism 313 or 413 can also facilitate removal of the portions 312$_i$ or 412$_i$, respectively, from the patient table when in the stored or retracted position.

Various embodiments employing the integrated coil design discussed herein (e.g., wherein one or more flexible coil arrays (e.g., 310, 410, 510, 520, 530, etc.) are stored in or under a spine coil array 210) have at least three advantages over existing systems. First, the thick cable connecting the flexible coil array (310, etc.) disappears from a MRI operator's workflow, because the flexible coils are connected to MRI system through the spine coil 210 or under the spine coil 210. Second, the workflow is similar to or better than with a wireless coil, because the operator simply does not see or interact with the wire anymore, and the flexible coil (310, etc.) only exists in the workflow when the operator wants to do imaging of the torso (e.g., for coil array 310, 410, 510) or other anatomical region (e.g., for coil arrays 520, 530, etc.). Third, the operator no longer needs to find the coil (310, etc.) anymore, because (when not in use) the flexible coil (310, etc.) is always under or in the spine coil 210 on the system table. Buttons, straps or other mechanical means (e.g., comprised within 313, 413, etc.) can be used to facilitate the flexible coils (310, etc.) being taken out of the patient table for imaging. Additionally, buttons, hook and loop fasteners, or other latching mechanisms can be used to wrap the flexible coil (310, etc.) around the torso, etc. and secure it in position for imaging. When the flexible coil (310, etc.) is retracted back to its storage position, a spring, elastic (e.g., rubber band, etc.) or other retraction mechanism (e.g., comprised within 316, 416, etc.) can be used to retract the coil (310, etc.) into openings 314$_i$ or 414$_i$ into the patient table within (as in FIG. 6) or under (as in FIG. 7) the spine coil array 210.

As can be seen in FIG. 5, discussed above, these techniques and corresponding advantages can be expanded from the torso to both the superior and inferior directions. In the inferior direction another (or another portion of the same) spine-like coil within the patient table can comprise or have underneath it a stored flexible coil 520 that can be used as a leg, knee and foot coil and/or for PV imaging. In the superior direction, another shorter (or another shorter portion of the same) spine-like coil can comprise or have underneath it a flexible coil 530 that can be used for head imaging. Additional mechanical fixture(s), such as head support 536, can be used to make the patient more comfortable. In some embodiments, these mechanical fixture(s) can be part of the spine-like coil or flexible coil 530. For head imaging, the flexible coil 530 can have several pre-set positions for different patient situations. As one example, for claustrophobic patients, it can be advantageous to cover the patient on the head side only and not the face side using the flexible coil 530, because covering the face of a claustrophobic patient may cause them distress. In various aspects, the mechanical fixture(s) (e.g., head support 536, etc.) can have a mechanical structure to facilitate the pre-set positions (e.g., by holding coil 530 in position, such as by coupling to corresponding structure(s) on coil 530, by clamping coil 530 in place at any selected position, etc.). If all three flexible coils 510, 520, and 530 are all within the patient table, then these coils can cover scanning from head to toe without need for any additional coils. In various embodiments, each of these flexible coils 510, 520, and 530 can be part of the patient table, and channel switching can be employed to disable the coil channels not being used during a current scan. In various embodiments, the three coils 510, 520, and 530 can be used for scanning head, torso, legs and PV/foot separately and/or simultaneously. As mentioned earlier, when flexible coils 510, 520, and 530 are not used, they can be stored underneath or within spine-like coils 210, and can be an integrated part of the patient table (e.g., wherein the flexible coils can be permanently electrically and mechanically connected to the patient table).

Examples herein can include subject matter such as a method, means for performing acts or blocks of the method, at least one machine-readable medium including executable instructions that, when performed by a machine (e.g., MRI machine, for example as described herein, etc.) cause the machine to perform acts of the method or of an apparatus or system according to embodiments and examples described.

A first example embodiment comprises a magnetic resonance imaging (MRI) radio frequency (RF) coil array comprising: a flat spine-like rigid (e.g., partly or wholly rigidly constructed, and/or partly or wholly held in a fixed position when employed as spine coil, etc.) array coil (e.g., spine coil array 210), and at least one flexible array coil (e.g., 310, 410, 510, 520, and/or 530), where the at least one flexible coil can be taken out to wrap around a patient for scanning at least one associated anatomical region, and can be retracted and stored underneath or inside the flat spine-like rigid array coil.

A second example embodiment comprises the first example embodiment, wherein the at least one flexible coil can be located at one side of the spine-like rigid array coil as one piece or located at both sides of the spine-like rigid array.

A third example embodiment comprises the second example embodiment, wherein the at least one flexible coil comprises more than one flexible coil along a superior and inferior direction.

A fourth example embodiment comprises the first example embodiment, wherein the at least one flexible coil can be disabled electrically when the coil is in stored condition.

A fifth example embodiment comprises the first example embodiment, wherein the at least one flexible coil comprises several spine-like coils that can be stored as flexible coils to cover leg and/or foot and/or head anatomies.

A sixth example embodiment comprises the first example embodiment, wherein each coil of the at least one flexible coil can be an integrated coil of the patient table so that no operator action is required to install that coil to the system.

A seventh example embodiment comprises the first example embodiment, wherein each flexible coil of the at least one flexible coil can be one of: a receiver coil in a receiver mode and decoupled from the whole body coil in a transmitter mode; a transmitter coil in a transmitter mode and a receiver coil in the receiver mode; or a coil inductively coupling to the whole body coil in the transmitter mode and a receiver coil in the receiver mode.

The following examples are additional embodiments.

Example 1 is a magnetic resonance (MR) imaging (MRI) radio frequency (RF) coil array configured to operate in at least one of a transmit (Tx) mode or a receive (Rx) mode, the MRI RF coil array comprising: at least one flat spine-like coil array configured to be arranged within a patient table of a MRI system; and at least one flexible coil array configured to be in a stored position within the patient table which can be either integrated into the table mechanically or separable from the table mechanically, wherein, in the stored position, the at least one flexible coil array is one of within or under the at least one flat spine-like rigid coil array, wherein the at least one flexible coil array is further configured to be in an extended position, wherein, in the extended position, the at least one flexible coil array is configured to be extracted from the patient table and to wrap around at least one anatomical region of a patient on the patient table to facilitate MRI of the at least one anatomical region.

Example 2 comprises the subject matter of any variation of any of example(s) 1, wherein, in the extended position, the at least one flexible coil array is configured to be extracted from the patient table via a single side of the patient table.

Example 3 comprises the subject matter of any variation of any of example(s) 2, further comprising at least one securing mechanism that is configured to mechanically connect the at least one flexible coil array in the extended position to an opposite side of the patient table from the single side.

Example 4 comprises the subject matter of any variation of any of example(s) 1, wherein, in the extended position, the at least one flexible coil array is configured to be extracted from the patient table via two opposite sides of the patient table.

Example 5 comprises the subject matter of any variation of any of example(s) 4, wherein a first flexible coil array of the at least one flexible coil array comprises a first set of array portions and a different second set of array portions, wherein the MRI RF coil array further comprises at least one securing mechanism that is configured to mechanically connect the first set of array portions to the second set of array portions when the at least one flexible coil array is in the extended position.

Example 6 comprises the subject matter of any variation of any of example(s) 1-5, wherein the at least one flexible coil array comprises a first flexible coil array and a different second flexible coil array that is offset from the first flexible coil array along a superior and inferior (SI) direction.

Example 7 comprises the subject matter of any variation of any of example(s) 1-6, wherein the at least one anatomical region comprises a torso, and wherein the at least one flexible coil array comprises a first flexible coil array configured to wrap around the torso to facilitate MRI of the torso.

Example 8 comprises the subject matter of any variation of any of example(s) 1-7, wherein the at least one anatomical region comprises legs, knees, and feet, and wherein the at least one flexible coil array comprises a first flexible coil array configured to wrap around the legs, knees, and feet to facilitate one or more of peripheral vascular imaging or MRI of at least one of the legs, knees, or feet.

Example 9 comprises the subject matter of any variation of any of example(s) 1-8, wherein the at least one anatomical region comprises a head, and wherein the at least one flexible coil array comprises a first flexible coil array configured to wrap around the head to facilitate MRI of the head.

Example 10 comprises the subject matter of any variation of any of example(s) 1-9, further comprising at least one disabling mechanism configured to electrically disable the at least one flexible coil array when the at least one flexible coil array is in the stored position.

Example 11 comprises the subject matter of any variation of any of example(s) 1-10, wherein the at least one flexible coil array is integrated into the patient table, wherein the at least one flexible coil array is permanently electrically and mechanically connected to the patient table.

Example 12 comprises the subject matter of any variation of any of example(s) 1-10, wherein the at least one flexible coil array is configured to be removably electrically and mechanically connected to the patient table.

Example 13 comprises the subject matter of any variation of any of example(s) 1-12, wherein a first flexible coil array of the at least one flexible coil array is a receive coil configured to operate when an associated MRI system operates in a receive mode and further configured to be disabled when the associated MRI system operates in a transmit mode.

Example 14 comprises the subject matter of any variation of any of example(s) 1-12, wherein a first flexible coil array of the at least one flexible coil array is a transmit/receive coil configured to operate when an associated MRI system operates in a receive mode and further configured to be one of inductively coupled to a whole body coil when the associated MRI system operates in a transmit mode or electrically connected to transmit circuitry when the associated MRI system operates in the transmit mode.

Example 15 comprises the subject matter of any variation of any of example(s) 1-14, further comprising at least one retraction mechanism that facilitates returning the at least one flexible coil array from the extended position to the storage position when the at least one flexible coil array is not in use.

Example 16 is a magnetic resonance imaging (MRI) radio frequency (RF) coil array configured to operate in at least one of a transmit (Tx) mode or a receive (Rx) mode, the MRI RF coil array comprising: at least one flat spine-like coil array configured to be arranged within a patient table of a MRI system; and at least one flexible coil array configured to be in a stored position within the patient table, wherein, in the stored position, the at least one flexible coil array is one of within or under the at least one flat spine-like rigid coil array, wherein the at least one flexible coil array is further configured to be in an extended position, wherein, in the extended position, a first flexible coil array of the at least one flexible coil array is configured to be extracted from the patient table and to wrap around a torso of a patient on the patient table to facilitate MRI of the torso.

Example 17 comprises the subject matter of any variation of any of example(s) 16, wherein, in the extended position, a second flexible coil array of the at least one flexible coil array is configured to be extracted from the patient table and to wrap around legs and feet of a patient on the patient table to facilitate at least one of peripherical vascular MRI or MRI of at least one of a leg, a knee, or a foot.

Example 18 comprises the subject matter of any variation of any of example(s) 16-17, wherein, in the extended position, a third flexible coil array of the at least one flexible coil array is configured to be extracted from the patient table and to wrap around a head of a patient on the patient table to facilitate MRI of the head.

Example 19 is a magnetic resonance imaging (MRI) apparatus, comprising: a patient table; and a magnetic resonance imaging (MRI) radio frequency (RF) coil apparatus configured to operate in at least one of a transmit (Tx) mode or a receive (Rx) mode, the MRI RF coil array comprising: at least one flat spine-like coil array configured to be arranged within the patient table of a MRI system; and at least one flexible coil array configured to be in a stored position within the patient table, wherein, in the stored position, the at least one flexible coil array is one of within or under the at least one flat spine-like rigid coil array, wherein the at least one flexible coil array is further configured to be in an extended position, wherein, in the extended position, the at least one flexible coil array is configured to be extracted from the patient table and to wrap around at least one anatomical region of a patient on the patient table to facilitate MRI of the at least one anatomical region.

Example 20 comprises the subject matter of any variation of any of example(s) 19, wherein, in the extended position, the at least one flexible coil array is configured to be extracted from the patient table via one of a single side of the patient table or two opposite sides of the patient table.

Example 21 is a MRI apparatus comprising a MRI RF coil array according to any variation of any of example(s) 1-20.

Circuits, apparatus, elements, MRI RF coils, arrays, methods, and other embodiments described herein are described with reference to the drawings in which like reference numerals are used to refer to like elements throughout, and where the illustrated structures are not necessarily drawn to scale. Embodiments are to cover all modifications, equivalents, and alternatives falling within the scope of the disclosure and appended claims. In the figures, the thicknesses of lines, layers and/or regions may be exaggerated for clarity. Nothing in this detailed description (or drawings included herewith) is admitted as prior art.

Like numbers refer to like or similar elements throughout the description of the figures. When an element is referred to as being "connected" to another element, it can be directly connected to the other element or intervening elements may be present. In contrast, when an element is referred to as being "directly connected" to another element, there are no intervening elements present. Other words used to describe the relationship between elements should be interpreted in a like fashion (e.g., "between" versus "directly between," "adjacent" versus "directly adjacent," etc.).

In the above description some components may be displayed in multiple figures carrying the same reference signs, but may not be described multiple times in detail. A detailed description of a component may then apply to that component for all its occurrences.

The following includes definitions of selected terms employed herein. The definitions include various examples or forms of components that fall within the scope of a term and that may be used for implementation. The examples are not intended to be limiting. Both singular and plural forms of terms may be within the definitions.

References to "one embodiment", "an embodiment", "various embodiments," "one example", "an example", or "various examples" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrases "in one embodiment" or "in various embodiments" does not necessarily refer to the same embodiment(s), though it may.

"Circuit", as used herein, includes but is not limited to hardware, firmware, or combinations of each to perform a function(s) or an action(s), or to cause a function or action from another circuit, logic, method, or system. Circuit can include a software controlled microprocessor, a discrete logic (e.g., ASIC), an analog circuit, a digital circuit, a programmed logic device, a memory device containing instructions, and other physical devices. A circuit can include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical logic between multiple physical circuits.

"Computer-readable storage device", as used herein, refers to a device that stores instructions or data. "Computer-readable storage device" does not refer to propagated signals. A computer-readable storage device can take forms, including, but not limited to, non-volatile media, and volatile media. Non-volatile media can include, for example, optical disks, magnetic disks, tapes, and other media. Volatile media can include, for example, semiconductor memories, dynamic memory, and other media. Common forms of a computer-readable storage device can include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store can store only A, only B, only C, A & B, A & C, B & C, and/or A & B & C). It is not intended to require one of A, one of B, and one of C. When the applicants intend to indicate "at least one of A, at least one of B, and at least one of C", then the phrasing "at least one of A, at least one of B, and at least one of C" will be employed.

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing the claims.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

In particular regard to the various functions performed by the above described components or structures (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations. In addition, while a particular feature may have been disclosed with respect to only one of several implementations, such feature can be combined with one or more other features of the other implementations as may be desired and advantageous for any given or particular application.

What is claimed is:

1. A magnetic resonance (MR) imaging (MRI) radio frequency (RF) coil array configured to operate in at least one of a transmit (Tx) mode or a receive (Rx) mode, the MRI RF coil array comprising:
   at least one flat spine-like coil array configured to be arranged one of within or above a patient table of a MRI system; and
   at least one flexible coil array configured to be in a stored position one of within or above the patient table, wherein, in the stored position, the at least one flexible coil array is the at least one flat spine-like coil array,
   wherein the at least one flexible coil array is further configured to be in an extended position, wherein, in the extended position, the at least one flexible coil array is configured to be extracted from the patient table and to wrap around at least one anatomical region of a patient on the patient table to facilitate MRI of the at least one anatomical region.

2. The MRI RF coil array of claim 1, wherein, in the extended position, the at least one flexible coil array is configured to be extracted from the patient table via a single side of the patient table.

3. The MRI RF coil array of claim 2, further comprising at least one securing mechanism that is configured to mechanically connect the at least one flexible coil array in the extended position to an opposite side of the patient table from the single side.

4. The MRI RF coil array of claim 1, wherein, in the extended position, the at least one flexible coil array is configured to be extracted from the patient table via two opposite sides of the patient table.

5. The MRI RF coil array of claim 4, wherein a first flexible coil array of the at least one flexible coil array comprises a first set of array portions and a second set of array portions different than the first set of array portions, wherein the MRI RF coil array further comprises at least one securing mechanism that is configured to mechanically connect the first set of array portions to the second set of array portions when the at least one flexible coil array is in the extended position.

6. The MRI RF coil array of claim 1, wherein the at least one flexible coil array comprises a first flexible coil array and a different second flexible coil array that is offset from the first flexible coil array along a superior and inferior (SI) direction.

7. The MRI RF coil array of claim 1, wherein the at least one anatomical region comprises a torso, and wherein the at least one flexible coil array comprises a first flexible coil array configured to wrap around the torso to facilitate MRI of the torso.

8. The MRI RF coil array of claim 1, wherein the at least one anatomical region comprises legs, knees, and feet, and wherein the at least one flexible coil array comprises a first flexible coil array configured to wrap around the legs, the knees, and the feet to facilitate one or more of peripheral vascular imaging or MRI of at least one of the legs, the knees, or the feet.

9. The MRI RF coil array of claim 1, wherein the at least one anatomical region comprises a head, and wherein the at least one flexible coil array comprises a first flexible coil array configured to wrap around the head to facilitate MRI of the head.

10. The MRI RF coil array of claim 1, further comprising at least one disabling mechanism configured to electrically disable the at least one flexible coil array when the at least one flexible coil array is in the stored position.

11. The MRI RF coil array of claim 1, wherein the at least one flexible coil array is integrated into the patient table, wherein the at least one flexible coil array is permanently electrically and mechanically connected to the patient table.

12. The MRI RF coil array of claim 1, wherein the at least one flexible coil array is configured to be removably electrically and mechanically connected to the patient table.

13. The MRI RF coil array of claim 1, wherein a first flexible coil array of the at least one flexible coil array is a receive coil configured to operate when an associated MRI system operates in a receive mode and further configured to be disabled when the associated MRI system operates in a transmit mode.

14. The MRI RF coil array of claim 1, wherein a first flexible coil array of the at least one flexible coil array is a transmit/receive coil configured to operate when an associated MRI system operates in a receive mode and further configured to be one of inductively coupled to a whole body coil when the associated MRI system operates in a transmit mode or electrically connected to transmit circuitry when the associated MRI system operates in the transmit mode.

15. The MRI RF coil array of claim 1, further comprising at least one retraction mechanism that facilitates returning the at least one flexible coil array from the extended position to the stored position when the at least one flexible coil array is not in use.

16. A magnetic resonance imaging (MRI) radio frequency (RF) coil array configured to operate in at least one of a transmit (Tx) mode or a receive (Rx) mode, the MRI RF coil array comprising:
   at least one flat spine-like coil array configured to be arranged one of within or above a patient table of a MRI system; and
   at least one flexible coil array configured to be in a stored position one of within or above the patient table, wherein, in the stored position, the at least one flexible coil array is within the at least one flat spine-like coil array,
   wherein the at least one flexible coil array is further configured to be in an extended position, wherein, in the extended position, a first flexible coil array of the at least one flexible coil array is configured to be extracted from the patient table and to wrap around a torso of a patient on the patient table to facilitate MRI of the torso.

17. The MRI RF coil array of claim 16, wherein, in the extended position, a second flexible coil array of the at least one flexible coil array is configured to be extracted from the patient table and to wrap around legs and feet of a patient on the patient table to facilitate at least one of peripherical vascular MRI or MRI of at least one of a leg, a knee, or a foot.

18. The MRI RF coil array of claim 16, wherein, in the extended position, a third flexible coil array of the at least one flexible coil array is configured to be extracted from the patient table and to wrap around a head of a patient on the patient table to facilitate MRI of the head.

19. A magnetic resonance imaging (MRI) apparatus, comprising:
- a patient table; and
- a MRI radio frequency (RF) coil array configured to operate in at least one of a transmit (Tx) mode or a receive (Rx) mode, the MRI RF coil array comprising:
  - at least one flat spine-like coil array configured to be arranged one of within or above the patient table of a MRI system; and
  - at least one flexible coil array configured to be in a stored position one of within or above the patient table, wherein, in the stored position, the at least one flexible coil array is within the at least one flat spine-like coil array,
  - wherein the at least one flexible coil array is further configured to be in an extended position, wherein, in the extended position, the at least one flexible coil array is configured to be extracted from the patient table and to wrap around at least one anatomical region of a patient on the patient table to facilitate MRI of the at least one anatomical region.

20. The MRI apparatus of claim 19, wherein, in the extended position, the at least one flexible coil array is configured to be extracted from the patient table via one of a single side of the patient table or two opposite sides of the patient table.

* * * * *